United States Patent [19]

Müller et al.

[11] Patent Number: 4,576,152

[45] Date of Patent: Mar. 18, 1986

[54] INJECTOR FOR BONE CEMENT

[75] Inventors: Maurice E. Müller, Berne; Otto Frey, Winterthur, both of Switzerland

[73] Assignee: Sulzer Brothers Limited, Winterthur, Switzerland

[21] Appl. No.: 543,238

[22] Filed: Oct. 18, 1983

[30] Foreign Application Priority Data

Oct. 21, 1982 [CH] Switzerland ............ 6118/82

[51] Int. Cl.$^4$ .............................. A61F 5/04
[52] U.S. Cl. ................... 128/92 R; 604/218; 128/92 E
[58] Field of Search ............ 128/92 R, 92 E; 604/218; 3/1.9

[56] References Cited

U.S. PATENT DOCUMENTS

| | | | |
|---|---|---|---|
| 2,709,436 | 5/1955 | Lynn | 604/218 |
| 3,223,083 | 12/1965 | Cobey | 128/92 R |
| 3,255,747 | 6/1966 | Cochran et al. | 128/92 R |
| 4,063,662 | 12/1977 | Drummond et al. | 604/218 |
| 4,277,184 | 7/1981 | Solomon | 128/92 R |
| 4,338,925 | 7/1982 | Miller | 128/92 E |
| 4,399,814 | 8/1983 | Pratt, Jr. et al. | 128/92 R |
| 4,462,394 | 7/1984 | Jacobs | 128/92 E |
| 4,466,435 | 8/1984 | Murray | 128/92 E |
| 4,488,549 | 12/1984 | Lee et al. | 3/1.9 |

FOREIGN PATENT DOCUMENTS

| | | |
|---|---|---|
| 0006408 | 1/1980 | European Pat. Off. . |
| 0023787 | 2/1981 | European Pat. Off. . |
| 0006430 | 3/1982 | European Pat. Off. . |
| 2827070 | 1/1980 | Fed. Rep. of Germany .... 128/92 R |
| 639549 | 11/1983 | Switzerland . |

Primary Examiner—Gene Mancene
Assistant Examiner—C. W. Shedd
Attorney, Agent, or Firm—Kenyon & Kenyon

[57] ABSTRACT

The injector is provided with an injection nozzle in the bottom of the cylinder tube for low pressure operation wherein large quantities of bone cement are to be injected. The injector also has a nozzle element which can be releaseably attached to the cylinder tube for high pressure injection. This nozzle element has a nozzle tube of reduced cross-sectional area through which a ram passes in the form of a piston in order to provide for high pressure injection.

8 Claims, 5 Drawing Figures

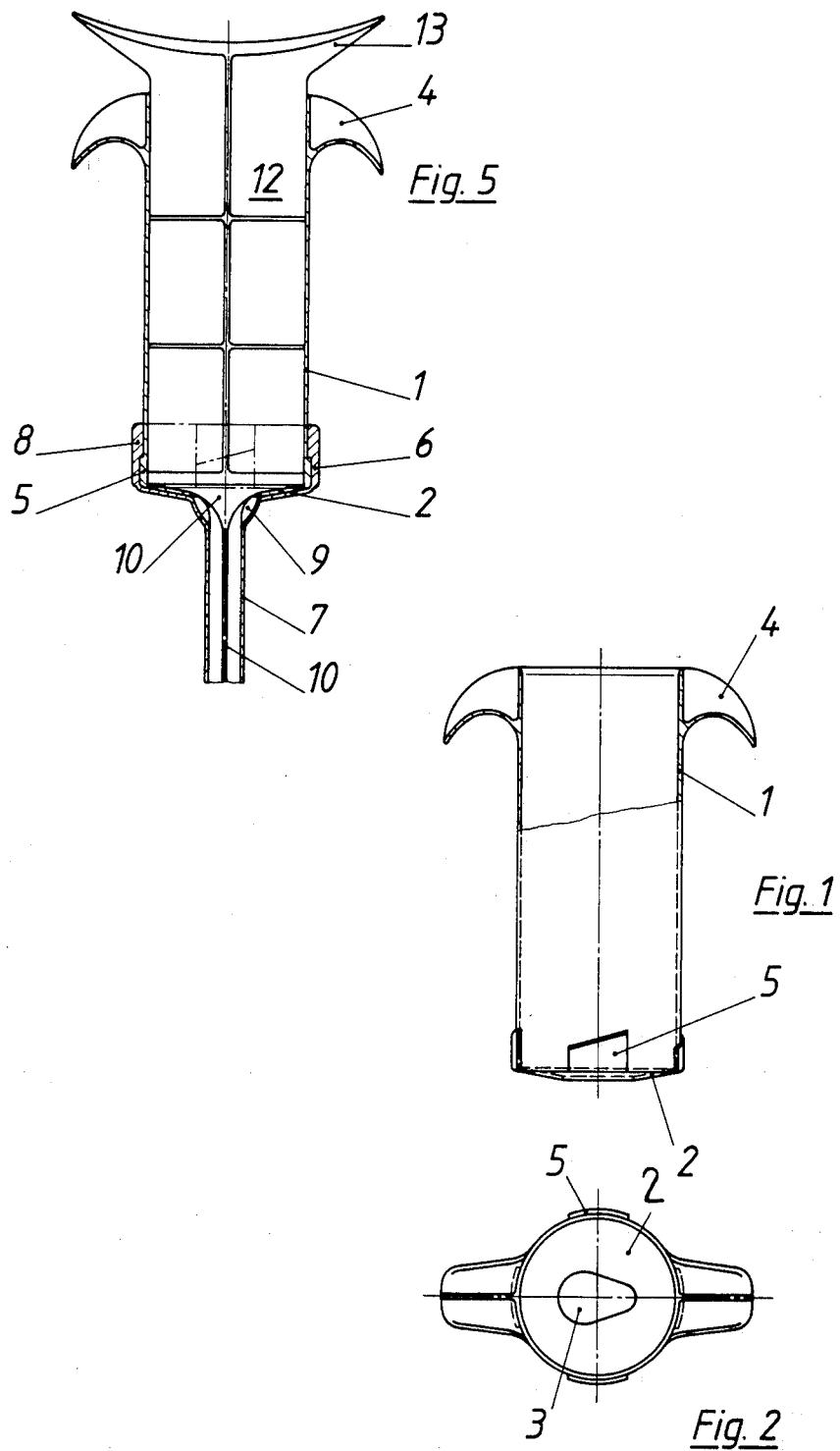

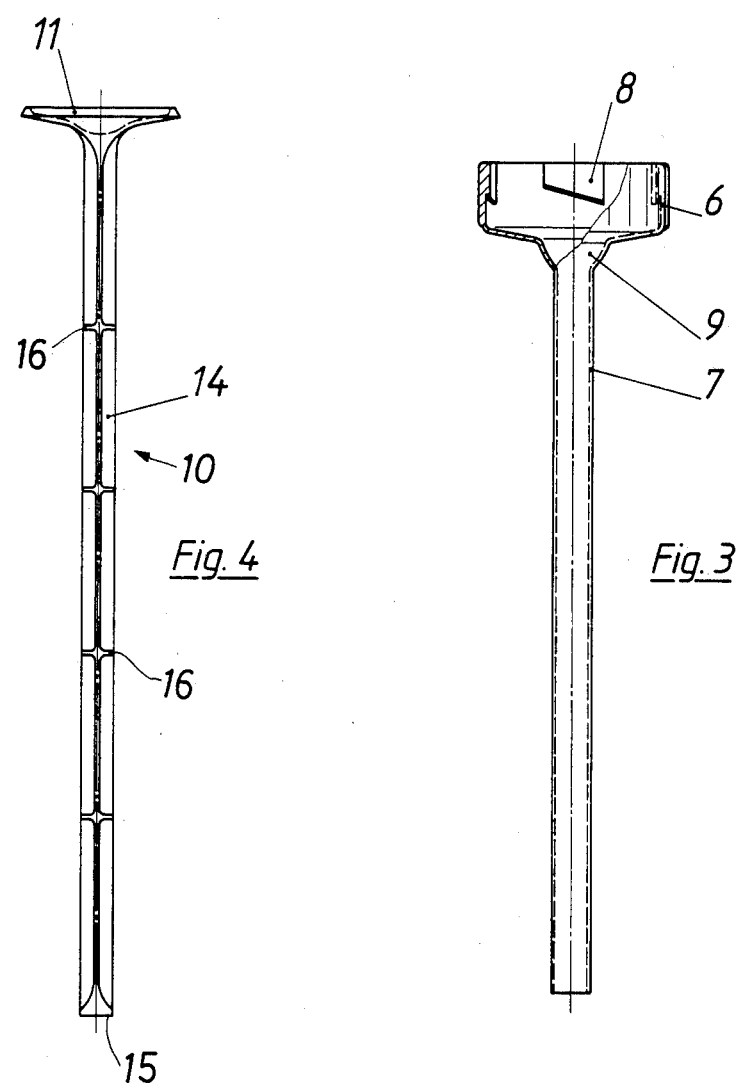

INJECTOR FOR BONE CEMENT

This invention relates to an injector for bone cement. More particularly, this invention relates to an injector for injecting expandable bone cement into a surgically prepared bone cavity.

Heretofore, various types of injectors or syringes have been known for injecting bone cement into surgically prepared bone cavities. For example, as described in European Patent B 1-006430, one known bone cement injector consists of a piston and cylindrical tube to which a nozzle element having a nozzle tube of relatively narrow cross-section is attached. Such an injector is constructed so as to permit the mixing and extrusion of a pasty bone cement in a simple manner. In this regard, the nozzle tube is made as a two-part member of relatively narrow cross-section.

As is known, during some surgical operations, it is necessary to inject a relatively large quantity of bone cement at relatively low pressure and thereafter to inject a small quantity of bone cement at relatively high pressure without applying substantially increased force. The injector described in the above noted European patent is, however, not capable of performing both a "low pressure" and a "high pressure" injection where the pressure is increased about twenty-fold.

Accordingly, it is an object of the invention to provide a bone cement injector which is capable of extruding a relatively large quantity of bone cement at relatively low pressure and of extruding a small quantity of bone cement at relatively high pressure.

It is another object of the invention to provide a bone cement injector which is capable of use for a low pressure injection and a high pressure injection.

It is another object of the invention to provide an injector which is capable of operating sequentially for injecting bone cement under low pressure and high pressure.

Briefly, the invention provides an injector for injecting an expandable bone implant cement. This injector is comprised of a cylinder tube for receiving the bone cement, a piston, a nozzle element and a ram. The cylinder tube is provided with a bottom and an injection nozzle in the bottom for expelling bone cement therethrough.

The piston is movably mounted in the cylinder tube for displacing bone cement in the tube through the injection nozzle.

The nozzle element is secured to and extends from the cylinder tube and has a nozzle tube aligned with and of smaller cross-section than the injection nozzle to pass bone cement therethrough.

The ram is movably mounted in the nozzle tube to eject bone cement therefrom. In this respect, the ram is displaceable in the manner of a piston in the nozzle tube.

In use, with the nozzle element removed, a relatively large quantity of bone cement can be extruded through the injection nozzle in the bottom of the cylinder tube. The injection of the bone cement can then take place under low pressure.

For a high pressure injection of bone cement into a bone cavity, the nozzle element is secured to the cylinder tube. At this time, the piston in the cylinder tube is used to fill the nozzle tube of the nozzle element with bone cement. Further, the ram serves to eject the bone cement from the filled nozzle tube. Of note, when the nozzle element is attached to the cylinder tube, the ram is guided through the cylinder tube and through the injection nozzle into the nozzle tube. Alternatively, the nozzle element can be detached from the cylinder tube and used as a separator injector.

The nozzle element can be secured to the cylinder tube in any suitable fashion, for example via a bayonet connection.

Further, the nozzle element may include a reservoir between the injection nozzle and the nozzle tube.

If the injector is to be used in a combined operational step both as a "high pressure" and as a "low pressure" injector, it is advantageous if the cylinder tube takes up the content of more than one standard package of bone cement, preferably two standard packages. For example, where a standard package contains about 50 to 60 cubic centimeters, generally about 55 cubic centimeters, of bone cement, the cylinder tube defines a volume of about 125 cubic centimeters for receiving the bone cement.

The ram may also be provided with a dish-type bearing plate at one end which can be attached to the piston within the cylinder tube. The advantage of this is that the entire bone cement injector can be evacuated without releasing the bayonet connection.

The bone cement injector is intended to be used only once. Hence, the injector may consist of a plastic which is common for such injectors, for example polymethyl pentene (TPX). In this case, the parts of the injector can be manufactured primarily by injection molding or as pressed parts.

These and other objects and advantages of the invention will become more apparent from the following detailed description taken in conjunction with the accompanying drawings wherein:

FIG. 1 illustrates a part cross-sectional view of a cylinder tube of an injector constructed in accordance with the invention;

FIG. 2 illustrates a top view of the cylinder tube of FIG. 1;

FIG. 3 illustrates a part cross-sectional view of a nozzle element constructed in accordance with the invention;

FIG. 4 illustrates a side view of a ram constructed in accordance with the invention; and FIG. 5 illustrates a partial view of an assembled injector in accordance with the invention.

Referring to FIG. 5, the injector for expelling bone cement is constructed of four parts namely, a tube 1 for receiving bone cement, a nozzle element 6, a ram 10 and a piston 12.

Referring to FIG. 1, the tube 1 is in the form of a cylinder and defines a volume of about 125 cubic centimeters for receiving bone cement, e.g. two standard packages of bone cement. The tube 1 has a bottom 2 which is slightly depressed conically in the center as well as an injection nozzle 3 (opening) which is formed substantially at the center of the bottom 2. The injection nozzle 3 is provided with a cross-sectional shape which is in rough approximation to the cross-sectional shape (see FIG. 2) of a shank of a femur head prosthesis (not shown). In addition, the upper end of the cylinder tube 1 is provided with two lateral flaps 4 which are arranged as abutments for the fingers of a hand. Further, the lower end of the cylinder tube 1 is provided with four rectangular reinforcements 5 which are distributed uniformly over the circumference of the tube 1. Each of the reinforcements 5 has an upper edge which is bevelled in the same direction so as to form part of a bayonet connection.

Referring to FIG. 3, the nozzle element 6 has a cylindrical cup-shaped portion at an upper end, as viewed, and an elongated nozzle tube 7. In addition, the cup-shaped portion has a plurality of circumferentially disposed inwardly directed projections 8 with bevelled lower edges. These projections 8 cooperate with the reinforcements 5 of the cylinder tube 1 in order to form a bayonet connection for securing the nozzle elements 6 in a releasable manner to the cylinder tube 1 as indicated in FIG. 5.

Referring to FIGS. 3 and 5, the nozzle element 6 also includes a reservoir 9 between the cup shaped portion and the nozzle tube 7. As indicated in FIG. 5, the reservoir 9 is located between the injection nozzle 3 and the nozzle tube 7 and is sized to have a volume of a few cubic centimeters.

Referring to FIG. 4, the ram 10 includes a dish type bearing plate 11 at an upper end, as viewed, and an elongated shank 14 of contoured cross-sectional shape. As indicated in FIG. 5, the bearing plate 11 is located within the cyliinder tube 1 above the bottom 3 and is of greater cross-sectional area than the cross-sectional area of the injection nozzle 3. The shank 14 of the ram 10 extends through the injection nozzle 3 and is adapted to the inside diameter of the nozzle tube 7 so as to function as a piston within the nozzle tube 7 during a "high pressure" injection. Of note, the bearing plate 11 is sized to a finger or thumb of a user. Further, the plate 11 may be attached to the piston 12 so that the piston 12 may be used to push the ram 10 within the cylinder tube 1 and through the nozzle tube 7.

Referring to FIG. 5, the piston 12 is of a diameter to slide within the cylinder tube in order to expel bone cement from the cylinder tube 1 through the injection nozzle 3. In addition, the piston 12 has hand grips 13 similar to the cylinder tube 1. These hand grips 13, in conjunction with the flaps 4 facilitate handling of the cement injector.

In order to use the injector for "low pressure" injection, the nozzle element 6 is removed. With bone cement filling the cylinder tube 1, the piston 12 can then be depressed so that the bone cement is expelled through the injection nozzle 3.

For "high pressure" injection, the nozzle element 6 is attached to the end of the cylinder tube 1 via the bayonet connection. As the piston 12 is then depressed, bone cement is expelled through the injection nozzle 3 into the reservoir 9 and then into the nozzle tube 7 which is of smaller cross-sectional area. As a result, the pressure on the bone cement increases without a significant increase in the force supplied to the piston 12. Since the shank 14 of the ram 10 extends through the injection nozzle 3, the shank 14 is suitably shaped in cross-section so as to permit the bone cement to be expelled. In this regard, it is noted that the cross-sectional area of the injection nozzle 3 is larger than the cross-sectional area of the shank 14 as well as the internal cross-sectional area defined by the nozzle tube 7.

Of note, it is possible to use both modes of use, each by itself as well as in combination. That is, first one and thereafter the other, in the same operational step.

The invention thus provides a bone cement injector which can be readily used for low pressure and high pressure injection in a simple manner.

Further, the invention provides an injector which can be used for low pressure injection where relatively large quantities of bone cement are required for injection into a bone cavity. Further, with the nozzle element attached, the injector can be used to inject relatively small quantities of bone cement at a high pressure, for example at approximately twenty times the low pressure.

It is the object of the reservoir 9 to soften the generation of whirls if the nozzle tube 7 has been mounted and the piston 12 is depressed down to the bottom 2.

The shank 14 of the ram 10 has a profile section as a cross. This cross profile ends in a piston-like circular end plate 15 (FIG. 4). Further spaced circular discs 16 (FIG. 4) interrupt the cross profile for stability of the shank and for guiding the ram 10 in the nozzle tube 7.

What is claimed is:

1. An injector for an expandable bone implant cement, said injector comprising
   a cylinder tube for receiving bone cement, said tube having a bottom and an injection nozzle in said bottom for expelling bone cement therethrough;
   a piston movably mounted in said tube for displacing bone cement in said tube through said injection nozzle;
   a nozzle element secured to and extending from said tube, said nozzle element having a nozzle tube aligned with and of smaller cross-section than said injection nozzle to pass bone cement therethrough; and
   a ram movably mounted in said nozzle tube to eject bone cement therefrom.

2. An injector as set forth in claim 1 wherein said nozzle element inlcudes a reservoir between said injection nozzle and said nozzle tube.

3. An injector as set forth in claim 1 wherein said cylinder tube defines a volume of about 125 cubic centimeters for receiving bone cement.

4. An injector as set forth in claim 1 wherein said nozzle element is removably secured to said tube.

5. An injector as set forth in claim 1 wherein said ram has a dish-type bearing plate at one end attached to said piston within said tube.

6. An injector for bone cement comprising
   a tube for receiving bone cement, said tube having a bottom and an injection nozzle in said bottom for expelling bone cement therethrough;
   a nozzle element removably secured to and extending from said tube, said nozzle element having a nozzle tube of smaller cross-section than said injection nozzle to pass bone cement therethrough;
   a ram movably mounted in said nozzle tube to eject bone cement therefrom, said ram having a bearing plate at one end within said tube and a shank extending from said bearing plate through said injection nozzle and into said nozzle tube; and
   a piston movably mounted in said tube for moving said ram into said nozzle tube while expelling bone cement through said injection nozzle.

7. An injector as set forth in claim 6 wherein said nozzle element includes a reservoir between said injection nozzle and said nozzle tube.

8. An injector as set forth in claim 6 having a bayonet connection removably securing said nozzle element to said tube.

* * * * *

UNITED STATES PATENT AND TRADEMARK OFFICE
CERTIFICATE OF CORRECTION

PATENT NO. : 4,576,152

DATED : March 18, 1986

INVENTOR(S) : Maurice E. Muller

It is certified that error appears in the above-identified patent and that said Letters Patent is hereby corrected as shown below:

On the title page assignee should read

--(73)Assignee: Sulzer Brothers Limited, Winterthur, Switzerland and Protek AG, Berne, Switzerland --.

Signed and Sealed this

Eleventh Day of November, 1986

Attest:

DONALD J. QUIGG

*Attesting Officer*   *Commissioner of Patents and Trademarks*